(12) United States Patent
Teramoto (10) Patent No.: US 7,018,202 B2
(45) Date of Patent: Mar. 28, 2006

(54) TOOTH MOVING METHOD AND APPLIANCE

(76) Inventor: Nobuhisa Teramoto, 396, Hatagawa, Kainan-shi Wakayama (JP)

( * ) Notice: Subject to any disclaimer, the term of this patent is extended or adjusted under 35 U.S.C. 154(b) by 160 days.

(21) Appl. No.: 10/358,302

(22) Filed: Feb. 5, 2003

(65) Prior Publication Data

US 2003/0157455 A1 Aug. 21, 2003

(30) Foreign Application Priority Data

Feb. 18, 2002 (JP) ............................. 2002-040111

(51) Int. Cl.
*A61C 3/00* (2006.01)

(52) U.S. Cl. .......................................... 433/18; 433/21
(58) Field of Classification Search .................. 433/18, 433/21, 22
See application file for complete search history.

(56) References Cited

U.S. PATENT DOCUMENTS 6,719,557 B1 * 4/2004 Williams ...................... 433/19

* cited by examiner

*Primary Examiner*—Kevin Shaver
*Assistant Examiner*—Candice C. Stokes
(74) *Attorney, Agent, or Firm*—Wenderoth, Lind & Ponack, L.L.P.

(57) ABSTRACT

A tooth moving method and appliance for securing a space for an incoming permanent tooth to arrive includes two lingual buttons to be fixed to two teeth, respectively, to spread out a space therebetween or correct a dentition therebetween. An inner wire is pivotally connected to a first lingual button at an end thereof, and a tube is loosely fitted onto the inner wire and pivotally connected to the other lingual button at an end thereof. An open coil is loosely fitted onto the tube, and a split stop is provided for adjusting the tensile force of the open coil. Thus the tensile force of the open coil is adjusted by the split stop to move at least either of the two teeth, so as to spread out the space therebetween to a desired extent.

9 Claims, 10 Drawing Sheets

TOOTH MOVING METHOD AND APPLIANCE

BACKGROUND OF THE INVENTION

1. Field of the Invention

The present invention relates to a tooth moving method and to a tooth moving appliance in an orthodontic clinic and the like.

2. Prior Art of the Invention

When a primary dentition is missed early, the teeth on both sides thereof move into the missing tooth space, resulting in narrowing or occupying of the space when an incoming permanent tooth arrives. As a result, the incoming permanent tooth is hindered from arriving (growing) at the right place, which causes disarrangement of the dentition. This problem not only spoils the occlusion, but also adversely affects the facial appearance.

To avoid this problem, when a primary dentition is missed early, a method using a molar distal moving appliance (stationary type), which is generally called "GMD (Greenfield Molar Distalizar), is generally used to secure the space to allow the incoming permanent tooth to arrive.

Figure 15:
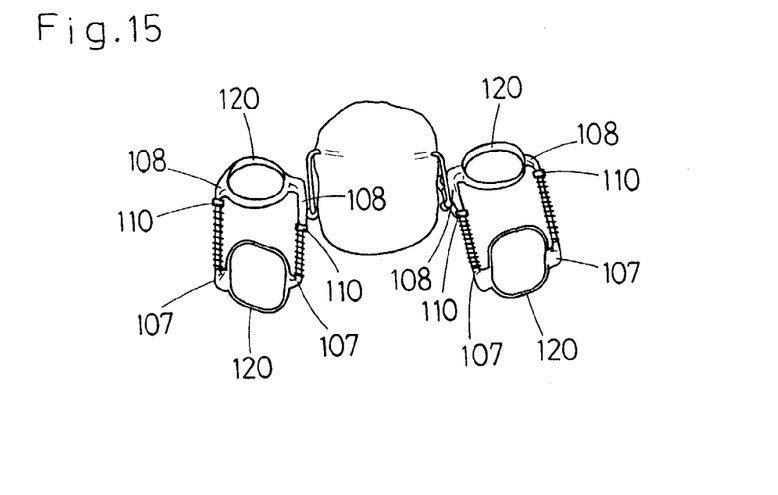
FIG. 15 is a front view of a tooth moving appliance according to the prior art.
Figure 16:
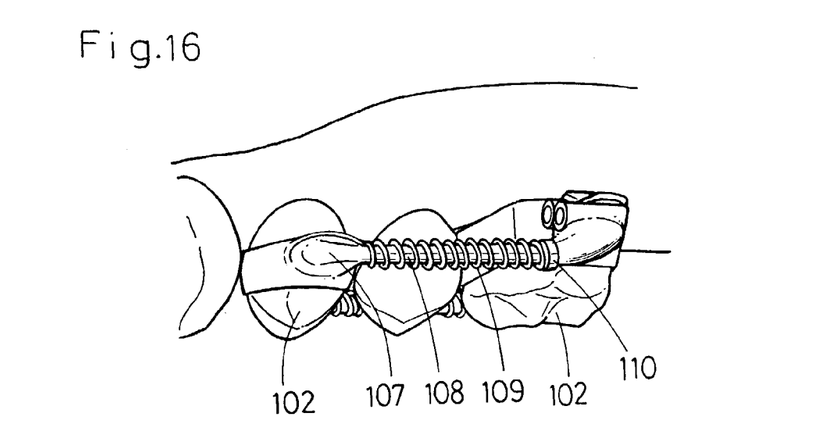
FIG. 16 is a side view of the tooth moving appliance according to the prior art which is in the fitted state.
Figure 17:
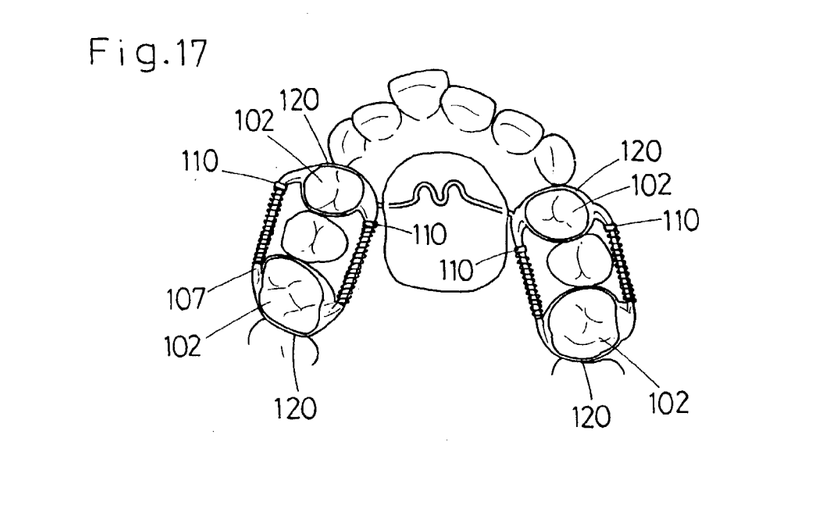
FIG. 17 is a front view of the tooth moving appliance according to the prior art which is in the fitted state.

This known molar distal moving appliance comprises, as shown in FIGS. 15–17, two seamless bands 120 to be fitted onto the teeth 102, 102, respectively, to spread out the space therebetween. Two inner wires 107 are arranged so that their ends are soldered to one of the bands 120 on the buccal side thereof and on the lingual side thereof, respectively. Two tubes 108 are loosely fitted onto the inner wires 107, and their ends are soldered to the other seamless band 120 on the buccal side thereof and on the lingual side thereof, respectively. Open coils 109 are loosely fitted onto the tubes 108, respectively, and tensile force of the open coils 109 is adjusted by means of split stops 110 to move at least either of the two teeth, so as to spread out the space to a desired extent or correct the dentition.

However, because of the configuration requiring that the inner wires and the tubes are firmly fixed to both seamless bands by soldering their ends to the buccal side of the seamless bands and on the lingual side of the same, this conventional type of molar distal moving appliance has the problem of taking much space in the mouth. Thus, a patient who fits the appliance on the teeth becomes uncomfortable or experiences pain.

Further, since the seamless bands must be accurately designed and made to fit onto each tooth of each individual patient, it is infeasible to make a stock production. For this reason, the conventional molar distal moving appliance must be made painstakingly piece by piece, requiring experience and skill and taking lots of time and labor, thus leading to the disadvantage of increased manufacturing costs.

In addition, the conventional molar distal moving appliance requires a high level of soldering technique for soldering the ends of the inner wires and tubes to the seamless bands, and also requires an expensive soldering device therefor. Thus, the conventional appliance involves increasing initial costs and running costs.

Moreover, since the ends of the inner wires and tubes are firmly soldered to the seamless bands fitted on the teeth, a moving direction of the seamless bands is limited to the direction for the inner wires and the tubes to be slid. This causes a problem in that when the conventional molar distal moving appliance is used, with its seamless bands fitted on the related teeth, a complicated and precise adjustment must be repeatedly made.

As mentioned above, in the conventional molar distal moving appliance, the ends of the inner wires and tubes are firmly soldered to the seamless bands. Consequently, the moving direction of the seamless bands is limited to the direction for the inner wires and the tubes to be slid. This causes a problem in that it is almost impossible to move an obliquely arriving (growing) tooth by using the conventional molar distal moving appliance.

Further, the conventional molar distal moving appliance has a fatal problem in that there is a possibility that the seamless bands themselves cannot be fitted onto the obliquely arriving teeth, depending on the degree of inclination of the tooth and the degree of growth of the tooth.

SUMMARY OF THE INVENTION

In the light of the problems mentioned above, the present invention has been made. It is an object of the present invention to provide a tooth moving method and appliance that is simple and less bulky in itself, easy to be fitted on the teeth, less burdensome for the patients, and can cut down initial costs and running costs.

To accomplish the object noted above, the present invention provides a tooth moving method wherein two lingual buttons are fixed to two teeth, respectively, to spread out a space therebetween or correct a dentition therebetween. An inner wire is pivotally connected to one of the two lingual buttons at an end thereof. A tube loosely fitted onto the inner wire is pivotally connected to the other lingual button at an end thereof, and an open coil is loosely fitted onto the tube. Thus, a compressive (pushing) force of the open coil is adjusted by a split stop to move at least either of the two teeth, so as to spread out the space therebetween to a desired extent.

In the tooth moving method, the end of the inner wire connected to its related lingual button and the end of the tube connected to its related lingual button are formed into a U-shape or a ring-like shape. The ends are fitted onto necks of their respective lingual buttons, and then are deformed to catch the necks, so that the ends are connected to their respective lingual buttons.

Also, the present invention provides a tooth moving appliance comprising two lingual buttons to be fixed to two teeth, respectively, to spread out a space therebetween to a desired extent or correct a dentition therebetween. A space-spreading biasing means is to be mounted between the two lingual buttons, and the space-spreading biasing means comprises an inner wire to be pivotally connected to one lingual button at an end thereof. A tube is to be loosely fitted onto the inner wire and pivotally connected to the other lingual button at an end thereof, and an open coil is loosely fitted onto the tube. A split stop is also provided for adjusting a pushing force of the open coil.

In the tooth moving appliance, the end of the inner wire connected to its related lingual button and the end of the tube connected to its related lingual button are formed into a U-shape or a ring-like shape so that after being fitted onto the necks of their respective lingual buttons, the end of the inner wire and the end of the tube can be deformed to catch their respective necks.

Accordingly, the present invention can provide the advantage of making the entire tooth moving appliance simple and less bulky in order to minimize an uncomfortable feeling or pain for the patient who fits the appliance in his/her teeth. This arrangement is to be compared with the conventional molar distal moving appliance having a configuration in which the inner wires and the tubes are fixed to the seamless bands, with their ends soldered to the seamless bands fitted on the teeth on the buccal side and on the lingual side, respectively. Further, according to the present invention, since the fitting of the tooth moving appliance onto the teeth can be practiced with ease at the location of the dental treatment, the components of the appliance can be produced in advance in large quantities. This can provide an additional advantage in that the manufacturing costs can be cut down drastically, differently from the conventional appliance that must be made painstakingly piece by piece, requiring experience and skill and taking lots of time and labor.

Moreover, according to the present invention, the connecting portions at which the inner wire and the tube are connected to their respective lingual buttons fixed to the teeth preserve such a certain degree of freedom of movement as to allow the inner wire and the tube to move toward the buccal side and the lingual side at the connecting portions. This can present comfort and fitness for the movement of each tooth of each individual patient, and, accordingly, can allow the teeth to always be biased in the direction for the teeth to be apart from each other, without complicated and precise adjustments and the like. This can provide the further advantage of providing enhanced dental treatment efficiency.

DETAILED DESCRIPTION OF THE PREFERRED EMBODIMENTS

In the following explanation, certain preferred embodiments of the present invention will be described with reference to the accompanying drawings.

A tooth moving appliance 1 comprises two lingual buttons 3, 3 to be fixed to two teeth 2, 2 for spreading out the space between the teeth, or for correcting the dentition between the teeth, and a space-spreading biasing means (biasing device) 4 mounted between the two lingual buttons 3, 3, as illustrated in FIG. 12.

Figure 1:
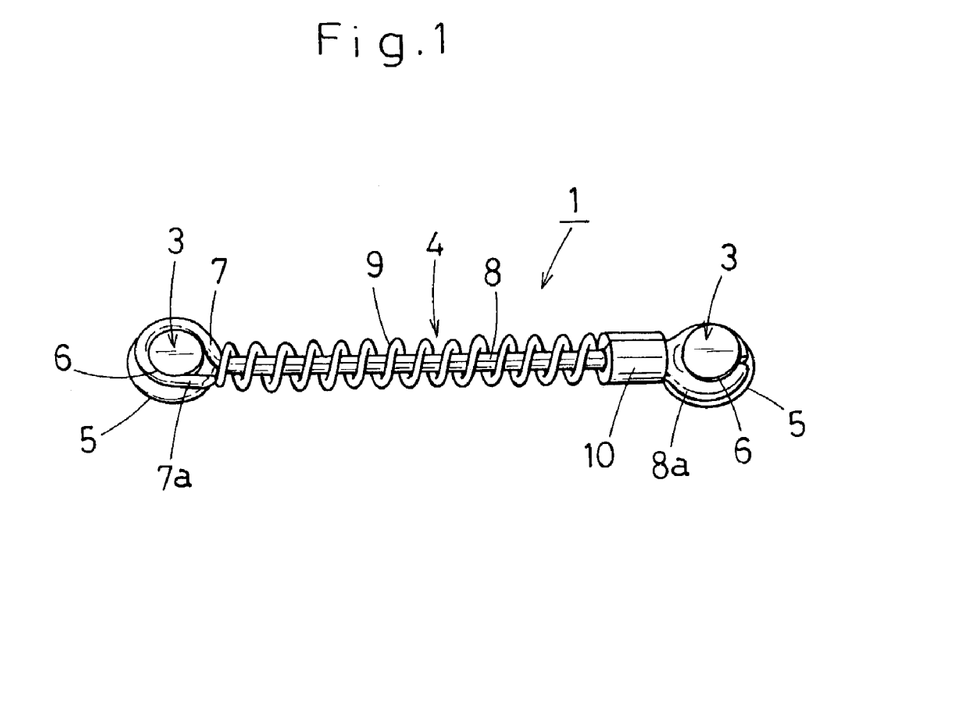
FIG. 1 is a front view of a tooth moving appliance according to the present invention.
Figure 2:
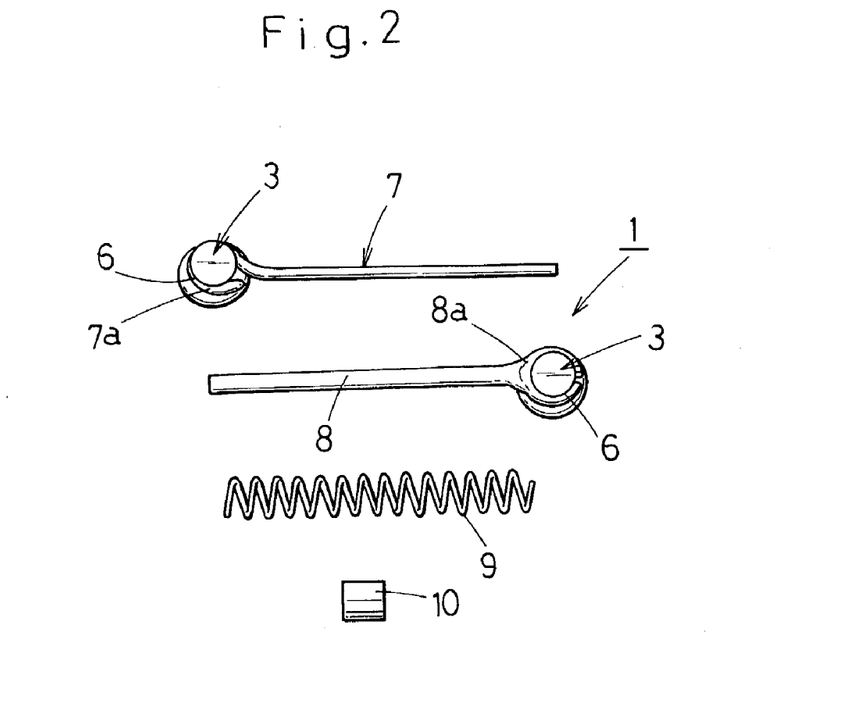
FIG. 2 is a view showing components of the tooth moving appliance according to the present invention.
Figure 3:
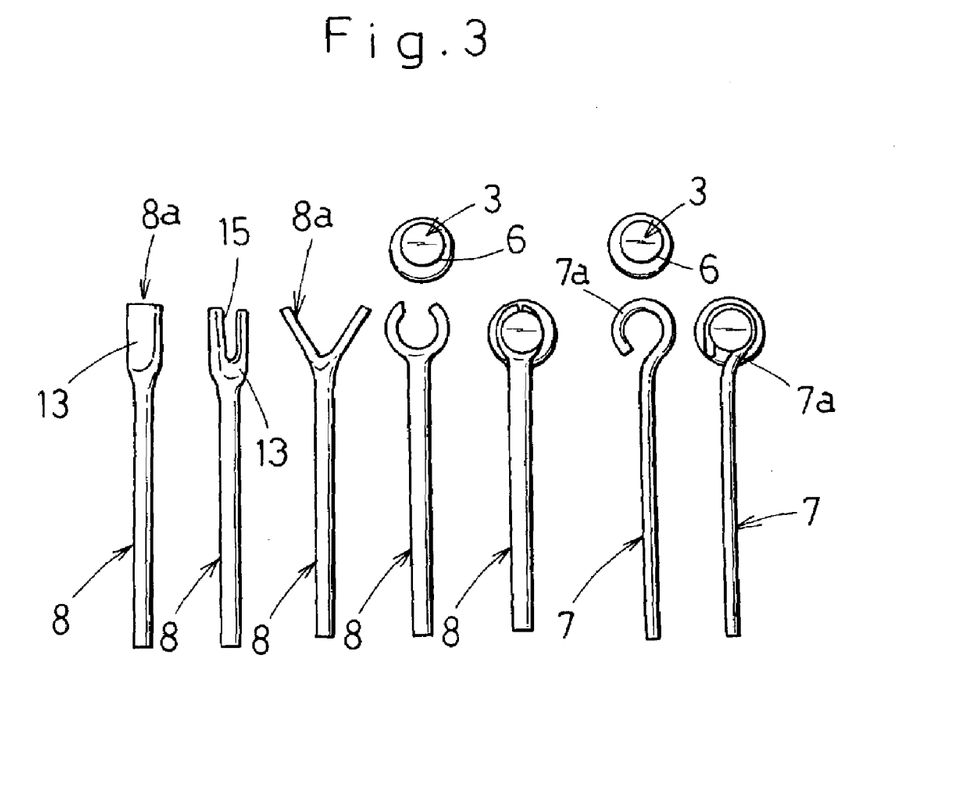
FIG. 3 is a development in the producing stage of parts of the tooth moving appliance according to the present invention.
Figure 4:
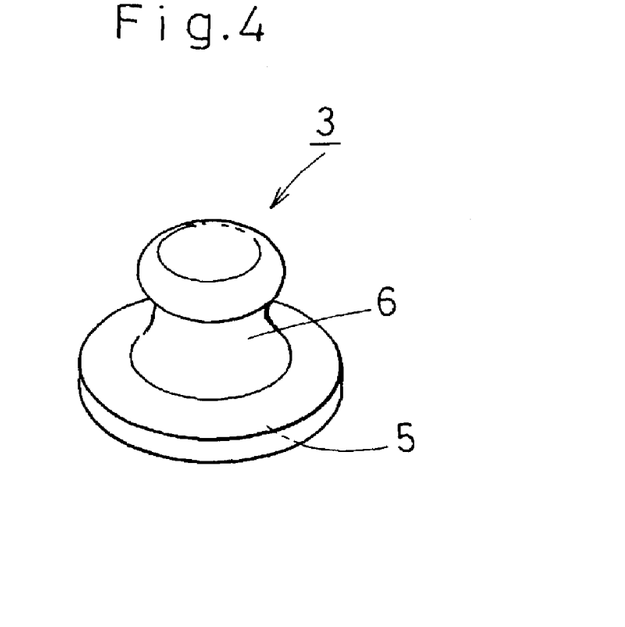
FIG. 4 is a perspective view of a lingual button of the tooth moving appliance according to the present invention.

The lingual buttons 3 are formed of rust-resistant metal such as stainless steel. Each lingual button 3 is formed to have in the bottom a stick-on surface 5 to be stuck on a tooth surface 2a of the tooth 2, and a neck 6 constricted at a portion thereof above the stick-on surface 5, as shown in FIG. 4. As shown in FIG. 4, the neck 6 has wider end portions and a narrower (constricted) middle portion.

The space-spreading biasing means (biasing device) 4 comprises an inner wire 7 to be pivotally connected to the narrow middle portion of the neck 6 of a first lingual button 3 at a base end 7a thereof; a tube 8 to be loosely fitted onto the inner wire 7 and pivotally connected to the neck 6 of the other (a second) lingual button 3 at a base 8a thereof; an open coil 9 to be loosely fitted onto the tube 8; and a split stop 10 for adjusting the tensile force of the open coil 9.

Figures 5A, 5B:
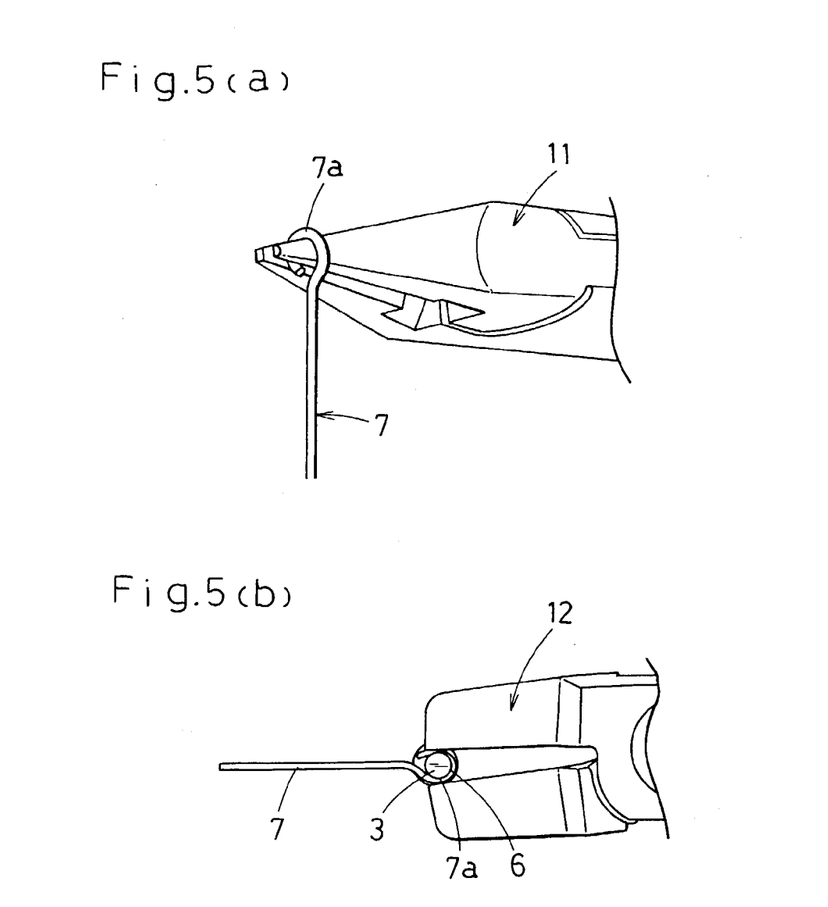
FIG. 5 illustrates fabrication processes of an inner wire of the tooth moving appliance according to the present invention.
Figure 6:
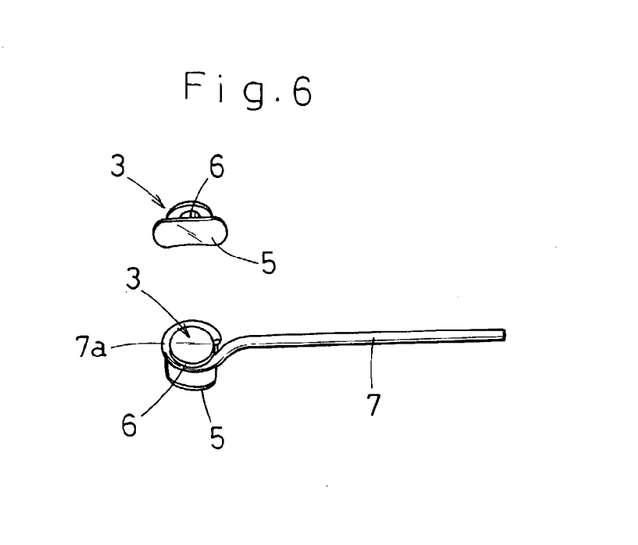
FIG. 6 is a perspective view showing the connection of the inner wire to the lingual button of the tooth moving appliance according to the present invention.

The inner wire 7 has a hook-shaped base end which is formed by turning the wire at an angle of nearly 360 degrees using a light wire plier 11 gripping a tip portion of the rust-resistant metal wire, such as stainless steel, of e.g. 0.7 mm in diameter (See FIG. 5a). The hook-shaped base end of the inner wire 7 is fitted onto the neck 6 of the first lingual button 3 from above and then is caulked by using an arch forming plier 12 to close the opening of the hook-shaped tip, as shown in FIGS. 5(a), (b). After this step, the base end 7a of the inner wire 7 is connected to the neck 6 of the first lingual button 3, while preserving a certain degree of freedom of movement (See FIG. 6).

Figure 7A:
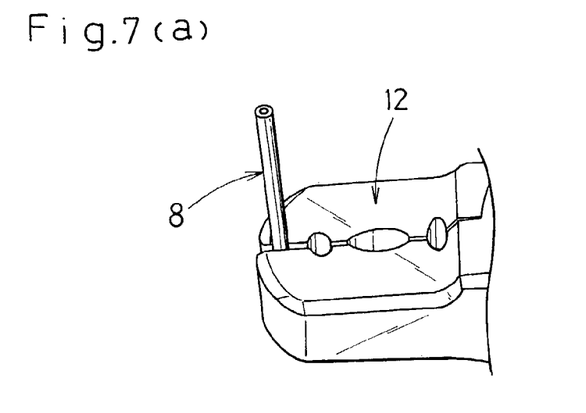
FIG. 7 illustrates fabrication processes of a tube of the tooth moving appliance according to the present invention.
Figure 7B:
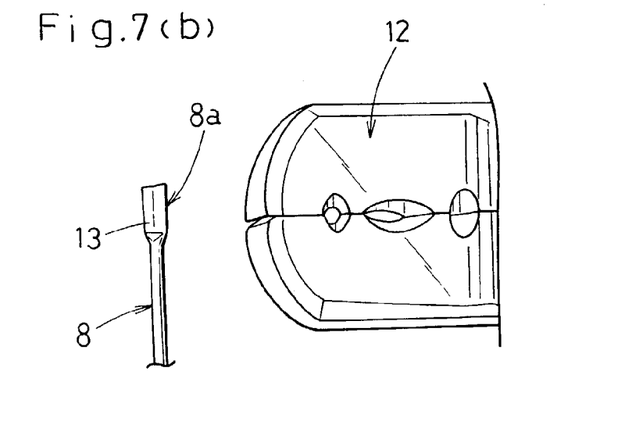

The tube 8 is produced in the following manner in the illustrated embodiment. First, a stainless steel tube having an inner diameter of 0.036 inch (about 0.9144 mm) (available from Ortho Dentrum, Item No. 480-009) is cut to a length of 17 mm, as shown in FIG. 7(a). Then, a base end portion 8a of the tube 8 on the side connected to the second lingual button 3 is flattened to within 3 mm from the tip by using a lingual bar bending plier 12 and the like, to form a flattened portion 13 (See FIG. 7(b)).

Figure 7C:
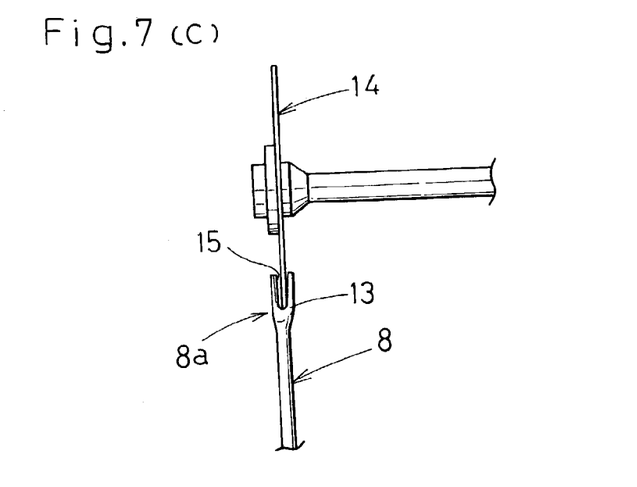
Figure 8A:
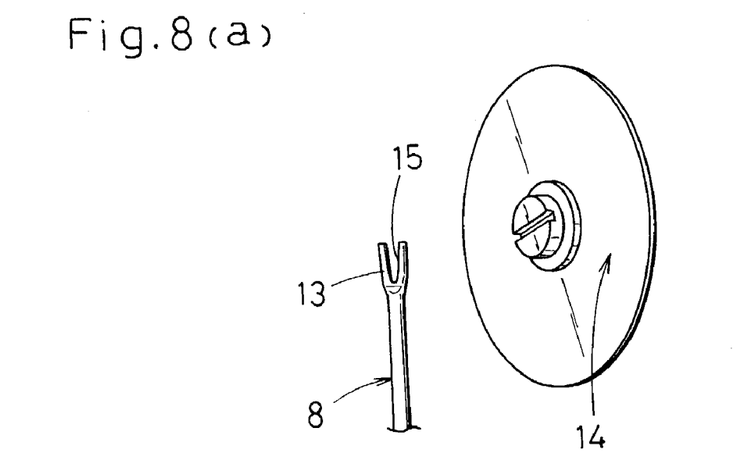
FIG. 8 illustrates fabrication processes of the tube of the tooth moving appliance according to the present invention.
Figure 8B:
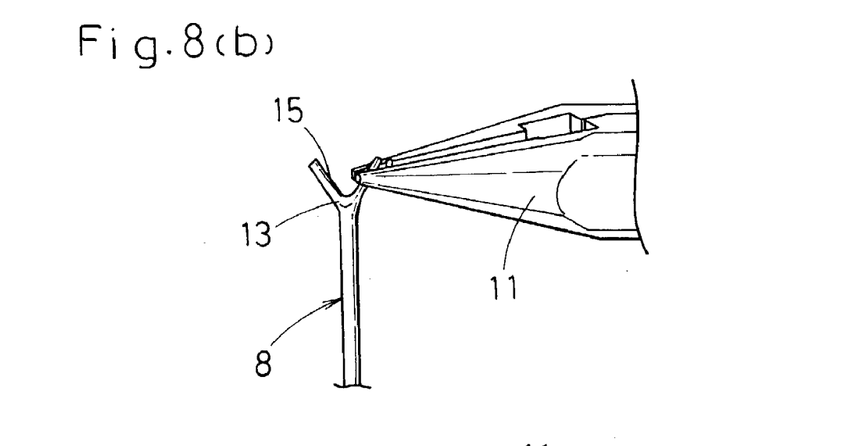
Figure 8C:
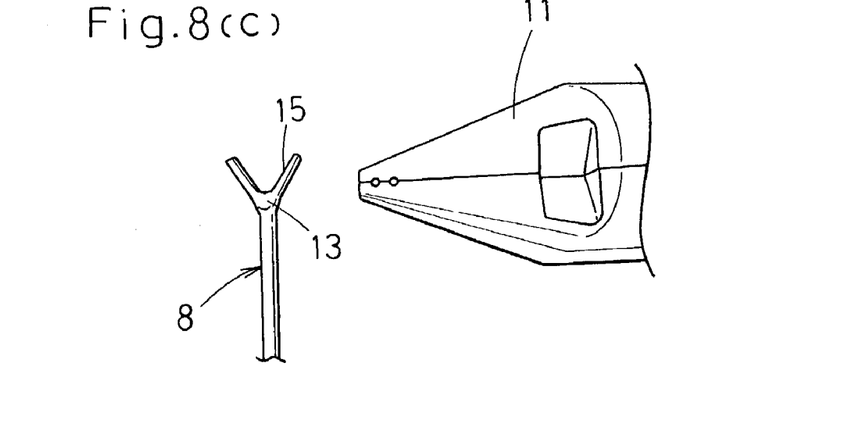
Figure 9A:
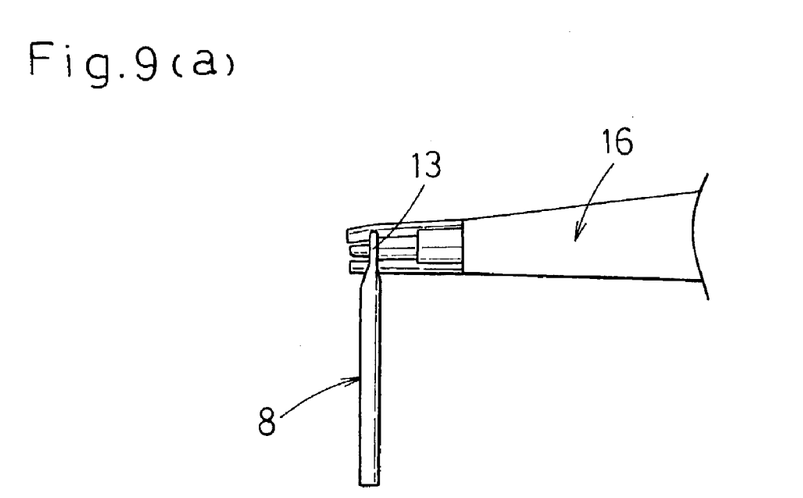
FIG. 9 illustrates fabrication processes of the tube of the tooth moving appliance according to the present invention.
Figure 9B:
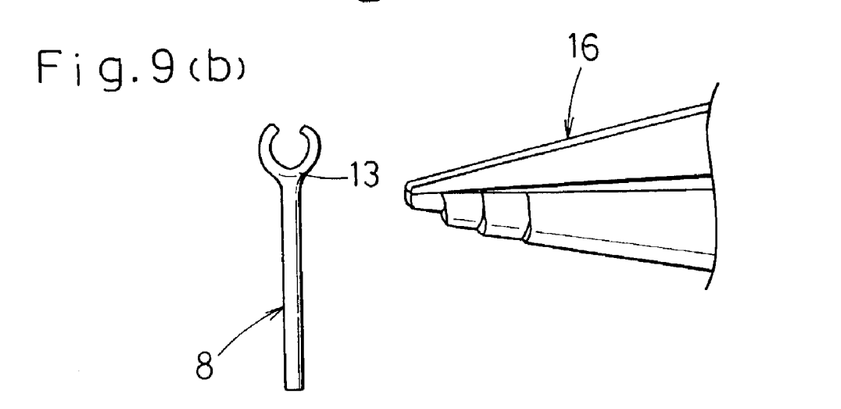

Then, the flattened portion 13 is slit up by using a disc cutter 14 and the like, to form a lengthwise slit 15 of a length of about 2.5 mm (See FIG. 7(c)). The end portion 8a thus slit up at 15 is then spread out in a Y-shape by using the light wire plier 11 (See FIGS. 8(b), (c)). The base end portion 8a thus spread out in Y-shape is curved into a C-shape having an opening at the top by using a loop forming plier 16, as shown in FIG. 9(a),(b).

Figure 9C:
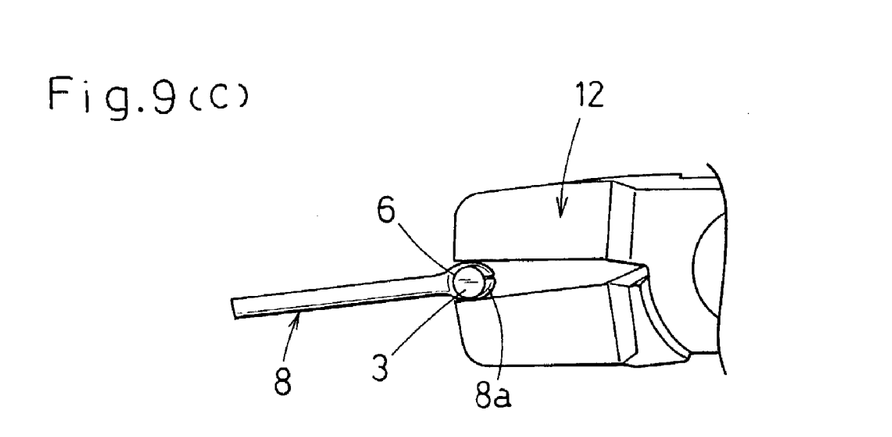
Figure 10:
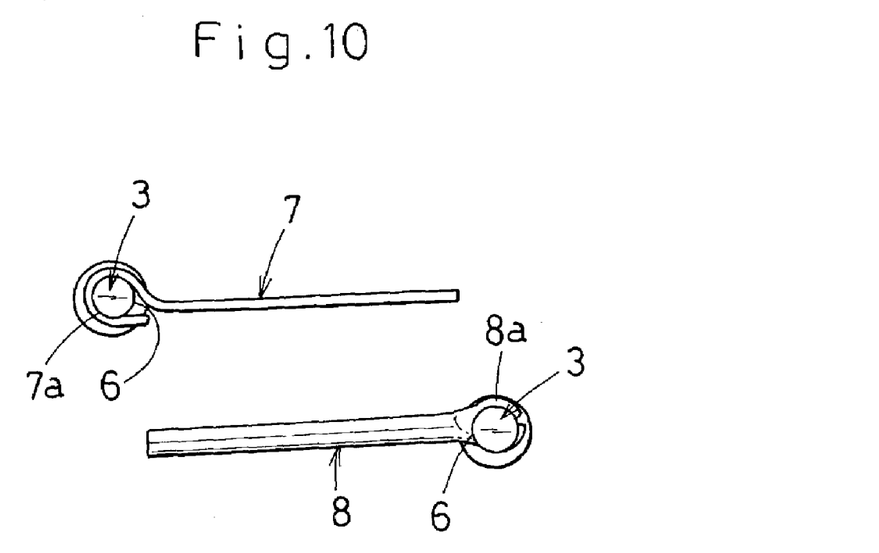
FIG. 10 is a perspective view of the inner wire and tube connected to their respective lingual buttons of the tooth moving appliance according to the present invention.

Thereafter, the base end portion 8a of the tube 8 thus C-shaped is fitted onto the neck 6 of the second lingual button 3, and the opening of the C-shaped base end portion 8a is closed by using the arch forming plier 12, as shown in FIG. 9(c). After this step, the base end portion 8a of the tube 8 is connected to the neck 6 of the second lingual button 3, while preserving a certain degree of freedom of movement, as shown in FIG. 10.

The open coil 9 is formed of a rust-resistant metal wire having elasticity, such as nickel titanium, and is formed into a coiled form having a length corresponding to the length of a tubular portion of the tube 8 loosely fitted onto the inner wire 7 (in this case, the difference of about 14 mm when about 3 mm of the length of the end portion 8a is subtracted from 17 mm of the total length of the tube 8).

Figure 11:
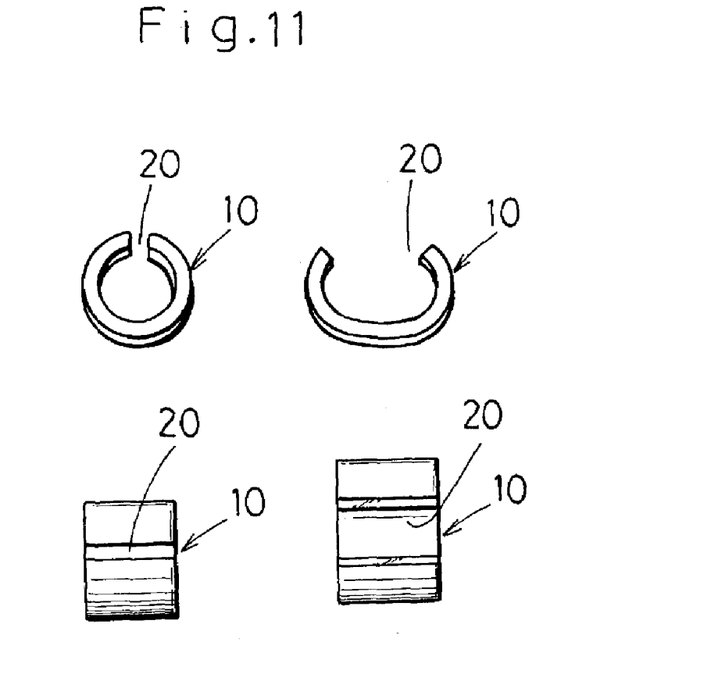
FIG. 11 is a drawing of a split stop of the tooth moving appliance according to the present invention.

The split stop 10 for adjusting the compression (pushing) force of the open coil 9 is formed as follows. First, a stainless steel tube having an inner diameter of 1.8 mm (available from Tomy Inc., Item No. 229-39) is slit up by using the disc cutter 14, to form a slit 20, as shown in FIG. 11. Then, the stainless steel tube thus slit up is cut in round slices of about 2 mm in width and then is spread out with its slit ends at 20 wide apart so as to fit onto the tubular portion of the tube 8.

Now, the procedure to move the teeth 2, 2 by using the tooth moving appliance 1 thus formed will be described.

Figure 12A:
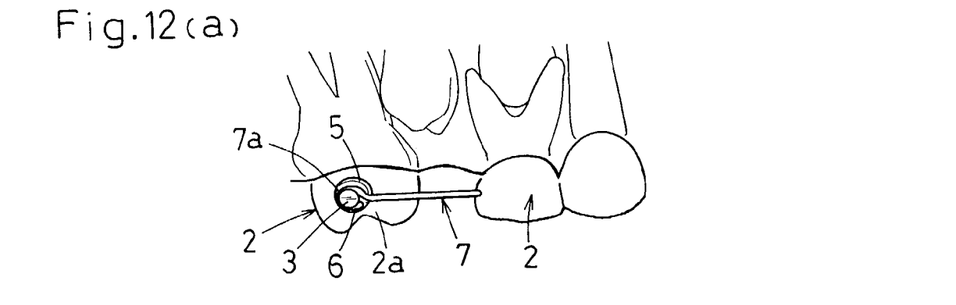
FIG. 12 illustrates the procedures for the use of the tooth moving appliance according to the present invention as viewed from the side.
Figure 12B:
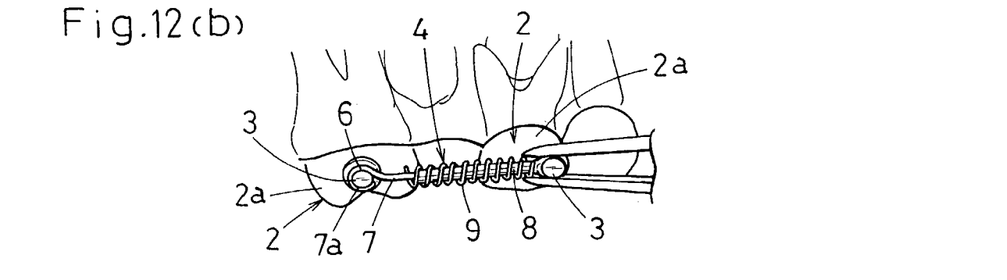

First, the stick-on surface 5 of the first lingual button 3 connected with the inner wire 7 is adhesive-bonded to the tooth surface 2a of one of the two teeth 2, 2 positioned on both sides of the missing tooth space produced when a primary dentition is missed early, and is fixed thereon, as shown in FIG. 12(a).

Then, the inner wire 7 is inserted into the tubular portion of the tube 8 loosely fitted in advance in the open coil 9. Thereafter, the second lingual button 3 attached to the tube 8 is adhesive-bonded to the tooth surface of the other tooth so as to be fixed thereon (See FIG. 12(b)). In other words, as illustrated in FIGS. 12(a) through 12(d), the tooth moving appliance 1 connects the two teeth located on the sides of a missing tooth space in either the upper jaw or the lower jaw (the upper jaw being illustrated in FIG. 12).

Figure 12C:
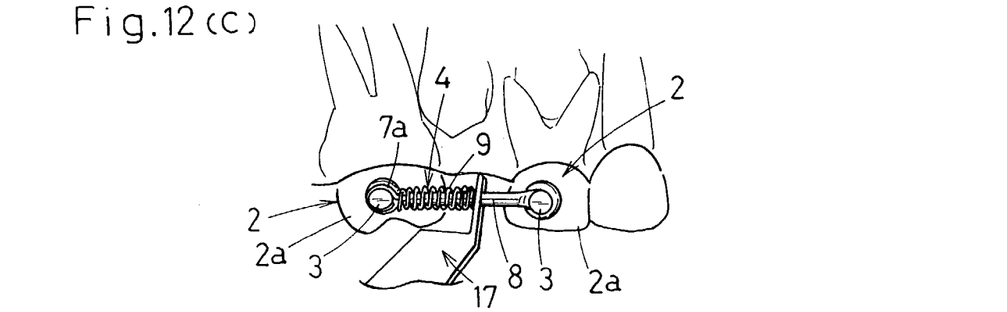
Figure 12D:
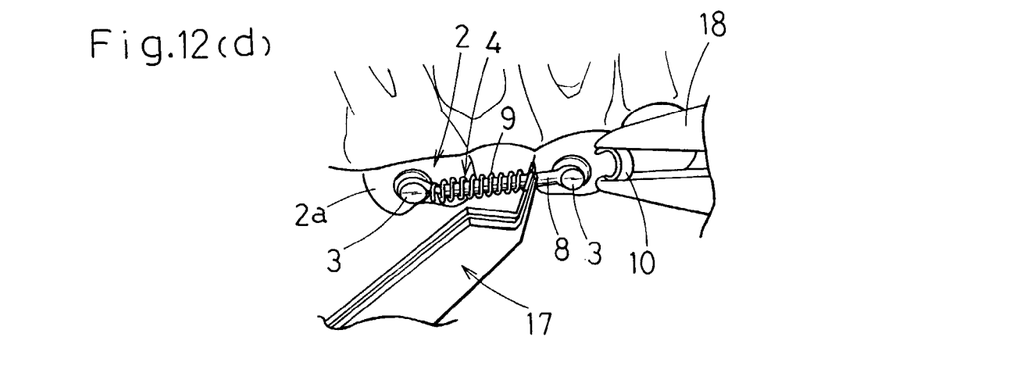

Then, the open coil 9 is compressed by pressing it toward the lingual button 3 of the inner wire 7 by using a pressing tool 17, to expose a part of the tubular portion of the tube 8, as shown in FIG. 12(c). Then, the split stop 10 is fitted onto the exposed part of the tubular portion of the tube 8, and is then caulked with the plier 18 to be fixed thereto, as shown in FIG. 12(d). Thereafter, the open coil 9 compressed with the pressing tool 17 is returned to its original position.

Figure 13:
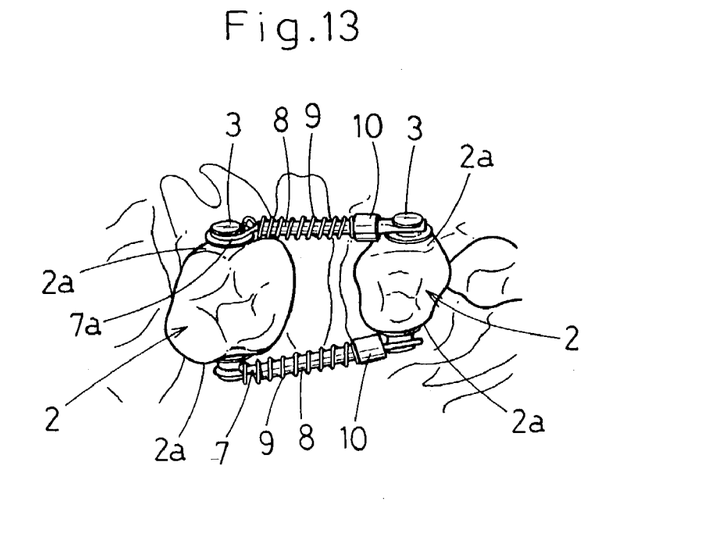
FIG. 13 is a front view of the tooth moving appliance according to the present invention which is in the fitted state.

When two tooth moving appliances 1 are fitted on the tooth surface on the buccal side and the tooth surface on the lingual side (one on each side) of the two teeth 2, 2 positioned on both sides of the missing tooth space produced when a primary dentition is missed early, respectively, both teeth 2, 2 are pressed with a predetermined pressure in the direction in which they are pushed apart from each other via the elastic force of the open coil 9 preset by the split stop 10 (See FIG. 13).

It is to be noted in this connection that the initial setting of the pressing force acting in the direction for both teeth 2, 2 to be pushed apart from each other and the change of the preset pressing force in the process of dental treatments can be made by changing or adjusting the number of split stops 10 and the width thereof. In other words, the amount of compression of coil 9 and, thus, the amount of pushing force applied by coil 9 can be adjusted by changing the number of split stops 10.

According to the present invention, the inner wire 7 and the tube 8 of the tooth moving appliance 1 are connected to the necks 6 of the lingual buttons 3, respectively, while preserving a certain degree of freedom of movement. This can provide an advantage in that for example, when a moving tooth 2 is observed as getting closer to the lingual side, an adjustment in the space spreading rate and an adjustment or correction in the dentition correcting direction can be made with ease by simply enhancing the elastic force of the open coil 9 by using an increased number of split stops 10 or a wider split stop 10 for the tooth moving appliance 1 on the lingual side.

While the preferred embodiment of the present invention has been illustrated above, it will be understood that the present invention should not be limited to the embodiment illustrated above, and various changes and modifications in design may be made in the invention within the scope of the claims.

Figures 14A, 14B:
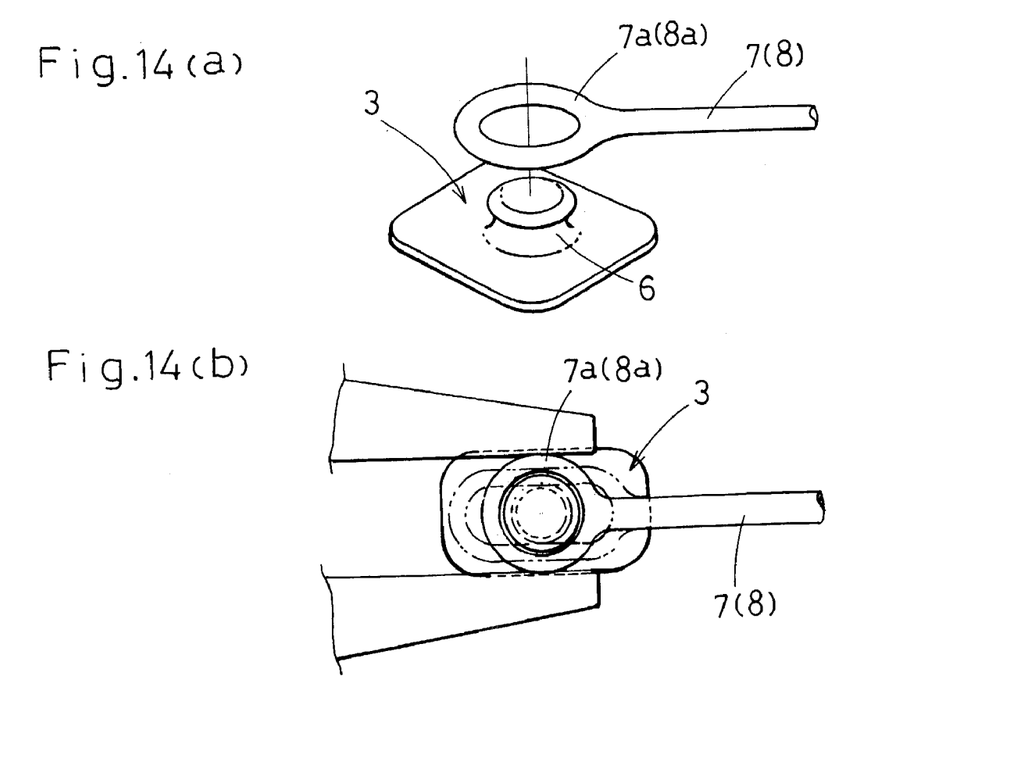
FIG. 14 is a diagram of a variant of the inner wire and tube to be connected to their respective lingual buttons of the tooth moving appliance according to the present invention.

For example, while in the illustrated embodiment, the connecting portion of the inner wire 7 to the lingual button 3 and the connecting portion of the tube 8 to the lingual button 3 are formed into the hook-shape and the C-shape having the opening at the top, respectively, those connecting portions may, of course, be formed into any suitable form without being limited to those forms. For instance, those connecting portions may be formed into a circular form or an oval form, or a polygonal ring-like form and deformed by caulking so as to be connected to the neck 6 of the lingual button 3, as shown in FIG. 14. Also, the inner wire 7 may, of course, be formed by a hollow wire without being limited to the solid wire.

What is claimed is:

1. A method of moving teeth, comprising:
   fixing a first button to a first tooth in one of an upper jaw and a lower jaw;
   fixing a second button to a second tooth in the one of the upper jaw and the lower jaw;
   pivotally connecting a basal end of an inner wire to the first button;
   fitting a tube onto the inner wire, and pivotally connecting a basal end of the tube to the second button;
   fitting an open coil onto the tube so that the open coil applies a pushing force against the first button and the second button so as to thereby apply a pushing force of separation against the first tooth and the second tooth; and
   adjusting the pushing force of the open coil using at least one stop fitted onto the tube.

2. The method of claim 1, further comprising:
   forming each of the basal end of the inner wire and the basal end of the tube into one of a U-shape and a ring-like shape;
   fitting the shaped basal end of the inner wire onto a neck of the first button and the shaped basal end of the tube onto a neck of the second button; and
   deforming the shaped basal end of each of the inner wire and the tube so as to catch and be connected to the first button and the second button, respectively.

3. The method of claim 1, wherein said adjusting the pushing force comprises changing a quantity of the at least one stop fitted onto the tube so as to change an amount of compression of the open coil.

4. The method of claim 3, wherein each of the at least one stop comprises a split ring-shaped stop fitted around the tube at an end of the open coil.

5. The method of claim 1, wherein said fixing of the first button to the first tooth comprises adhesive-bonding a surface of the first button to the first tooth, and said fixing of the second button to the second tooth comprises adhesive-bonding a surface of the second button to the second tooth.

6. A tooth-moving apparatus comprising:
   a first button to be fixed to a first tooth in one of an upper jaw and a lower jaw;
   a second button to be fixed to a second tooth in the one of the upper jaw and the lower jaw; and
   a biasing device to be mounted to said first button and said second button, said biasing device including:
      an inner wire having a basal end to be pivotally connected said first button;

a tube to be fitted onto said inner wire, and having a basal end to be pivotally connected to said second button;

an open coil to be fitted onto said tube so as to apply a pushing force against said first button and said second button so as to thereby apply a pushing force of separation against the first tooth and the second tooth; and at least one stop to be fitted onto said tube for adjusting the pushing force applied by said open coil against said first button and said second button, wherein each of said first button and said second button has a neck said neck of each of said first button and said second button having wide end portions and a narrower middle portion between said wide end portions, said basal end of said inner wire being connected to said narrower middle portion of said neck of said first button, and said basal end of said tube being connected to said narrower middle portion of said neck of said second button.

7. The apparatus of claim 6, wherein each of said basal end of said inner wire and said basal end of said tube has one of a U-shape and a ring-like shape, and said shaped basal end of said inner wire is to be fitted onto said neck of said first button and said shaped basal end of said tube is to be fitted onto said neck of said second button.

8. The apparatus of claim 6, wherein said at least one stop comprises a plurality of stops fitted onto said tube so as to change an amount of compression of said open coil.

9. The apparatus of claim 6, wherein each of said at least one stop comprises a split ring-shaped stop fitted around said tube at an end of said open coil.

* * * * *